(12) United States Patent
Kamins et al.

(10) Patent No.: US 7,570,355 B2
(45) Date of Patent: Aug. 4, 2009

(54) NANOWIRE HETEROSTRUCTURES AND METHODS OF FORMING THE SAME

(75) Inventors: Theodore I. Kamins, Palo Alto, CA (US); Alexandre M. Bratkovski, Mountain View, CA (US); Shashank Sharma, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 605 days.

(21) Appl. No.: 11/341,705

(22) Filed: Jan. 27, 2006

(65) Prior Publication Data

US 2007/0177139 A1    Aug. 2, 2007

(51) Int. Cl.
G01J 3/44 (2006.01)
G01N 21/65 (2006.01)

(52) U.S. Cl. .................................... 356/301
(58) Field of Classification Search .............. 356/301
See application file for complete search history.

(56) References Cited

U.S. PATENT DOCUMENTS

| | | | |
|---|---|---|---|
| 6,128,214 A | 10/2000 | Kuekes et al. | |
| 6,294,450 B1 | 9/2001 | Chen et al. | |
| 6,383,923 B1 | 5/2002 | Brown et al. | |
| 6,465,132 B1 | 10/2002 | Jin | |
| 6,861,263 B2 | 3/2005 | Natan | |
| 6,882,051 B2 | 4/2005 | Majumdar et al. | |
| 7,402,531 B1 * | 7/2008 | Kuekes et al. | 356/301 |
| 2002/0172820 A1 | 11/2002 | Majumdar et al. | |
| 2002/0175408 A1 | 11/2002 | Majumdar et al. | |
| 2003/0042128 A1 | 3/2003 | Harutyunyan et al. | |
| 2003/0089899 A1 | 5/2003 | Lieber et al. | |
| 2004/0075464 A1 | 4/2004 | Samuelson et al. | |

OTHER PUBLICATIONS

Gudiksen, Mark S., et al., "Growth of nanowire superlattice structures for nanoscale photonics and electronics," Nature, vol. 415, pp. 617-620 (Feb. 7, 2002).

Hicks, Christine J., "SERS, Surface Enhanced Raman Spectroscopy," pp. 1-8, Spring 2001.

Kim, Hong Koo, "Self-Organized Nanostructures-on-Wafers with Controlled Symmetry and Order," Power Point Presention, Intellectual Property/University of Pittsburgh, 27 pages, Sep. 2002.

Kneipp, K., et al., "Single-molecule Raman spectroscopy—fact or fiction?," Chimia 1999; 53 (1/2): 35-37.

Liang, Jianyu, et al., "Nonlithographic Fabrication of Lateral Superlattices for Nanometric Electromagnetic-Optic Applications," IEEE Journal of Selected Topics in Quantum Electronics, vol. 8, No. 5, pp. 998-1008, Sep./Oct. 2002.

(Continued)

Primary Examiner—F. L Evans

(57) ABSTRACT

A NERS-active structure is disclosed that includes at least one heterostructure nanowire. The at least one heterostructure nanowire may include alternating segments of an NERS-inactive material and a NERS-active material in an axial direction. Alternatively, the alternating segments may be of an NERS-inactive material and a material capable of attracting nanoparticles of a NERS-active material. In yet another alternative, the heterostructure nanowire may include a core with alternating coatings of an NERS-inactive material and a NERS-active material in a radial direction. A NERS system is also disclosed that includes a NERS-active structure. Also disclosed are methods for forming a NERS-active structure and methods for performing NERS with NERS-active structures.

20 Claims, 11 Drawing Sheets

OTHER PUBLICATIONS

Lieber, Charles M., "Nanowire Superlattices," Nano Lett., vol. 2, No. 2, pp. 81-82, Feb. 2002.

Michaels, Amy M., et al., "Surface Enhanced Raman Spectroscopy of Individual Rhodamine 6G Molecules on Large Ag Nanocrystals," J. Am. Chem. Soc., vol. 121, No. 43, pp. 9932-9939, 1999.

Pena, David J., et al., "Template Growth of Photoconductive Metal—CdSe—Metal Nanowires," J. Phys. Chem. B, vol. 106, No. 30, pp. 7458-7462, 2002.

Willatzen, M., et al., "Quantum confinement phenomena in nanowire superlattice structures," Mathematics and Computers in Simulation 65, pp. 385-397, 2004.

Wu, Yiying, et al., "Block-by-Block Growth of Single-Crystalline Si/SiGe Superlattice Nanowires," Nano Lett., vol. 2, No. 2, pp. 83-86, 2002.

Y Wu et al-"Single-crystal metallic nanowires and metal/semiconductor nanowire heterostructures"-Nature-vol. 430 No. 6995-Jul. 1, 2004-pgs 61-65.

D C Bell et al-"Imaging and analysis of nanowires"-Microscopy Research and Technique 2004-vol. 64 No. 5-6-pp. 373-389.

K Kneipp et al-"Surface-enhanced and normal stokes and anti-stokes Raman spectroscopy of single-walled carbon nanotubes"-Phys Rev Letts vol. 84 No. 15-Apr. 10, 2000-pp. 3470-3473.

M Law et al-"Semiconductor Nanowires and nanotubes"-Annual Review of Maaterials Science vol. 24-2004-pp. 83-122.

Hung-Min Lin et al-"Growth and Optical Properties of GaP , GaP GaN and GaN GaP Core-Shell Nanowires"-Proc Materials Research Socirty Symposium 2003-vol 776-pp. 23-30.

Meng et al-"Synthesis and Raman scattering of Beta0SiC.Si02 core-shell nanowires"-Journal of Srystal Growth vol. 308 No. 2 Oct. 15, 2007-pp. 263-268.

Katrin Kneipp et al-"Surface-enhance Raman scattering on single-wall carbon nanotubes"-Philosophical Transactions Series A vol. 362 No. 1824 Nov. 15, 2004-pp. 2361-2373.

G Sauer et al-"Surface-enhanced Raman spectroscopy employing monodisperse nickel nonowire arrays"-Applied Physics Letters vol. 88 No. 2 Jan. 10, 2006-pp. 23106 . . . .

US 6,780,301, 08/2004, Natan et al. (withdrawn)

* cited by examiner

NANOWIRE HETEROSTRUCTURES AND METHODS OF FORMING THE SAME

FIELD OF THE INVENTION

The invention relates to nano-enhanced Raman spectroscopy (NERS). More particularly, the invention relates to NERS-active structures including features having nanoscale dimensions, methods for forming NERS-active structures, and methods for performing NERS using NERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation are detected by a detector, such as a photomultiplier or a wavelength-dispersive spectrometer, which converts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency. This unique Raman spectrum may be used for many purposes, such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to conventional Raman spectroscopy. In SERS, the analyte molecules are adsorbed onto, or placed adjacent to, a Raman-active metal surface or structure (a "SERS-active structure"). The interactions between the molecules and the structure cause an increase in the strength of the Raman signal. The mechanism of Raman signal enhancement exhibited in SERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," J. Am. Chem. Soc. 121, 9932-39 (1999)).

Several SERS-active structures have been employed in SERS techniques, including active electrodes in electrolytic cells, active metal colloid solutions, and active metal substrates such as a roughened metal surface or metal "islands" formed on a substrate. For example, it has been shown that adsorbing analyte molecules onto or near a specially roughened metal surface made from gold or silver may enhance the effective Raman scattering intensity by factors of between $10^3$ and $10^6$ when averaged over the illuminated area of the sample.

Recently, Raman spectroscopy has been performed employing randomly oriented nanostructures, such as nanometer scale needles, particles, and wires, as opposed to a simple roughened metallic surface. This process will be referred to hereinafter as NERS. The intensity of the Raman scattered photons from a molecule adsorbed on such a nanostructure may be increased by factors as high as $10^{14-16}$. Thus, the intensity of Raman scattered photons could be increased over what is obtained presently if there was a method for forming NERS-active structures that included nanoscale features having well controlled size, shape, location, and orientation. Also, the inability to efficiently produce such NERS-active structures is impeding research directed to completely understanding the enhancement mechanisms and, therefore, the ability to optimize the enhancement effect. In addition, NERS-active structures require significant time and money to fabricate. If these problems can be overcome, the performance of nanoscale electronics, optoelectronics, and molecular sensors may be significantly improved.

Accordingly, there is a need for NERS-active structures that include nanoscale features having well controlled size, shape, location, and orientation, and methods for their manufacture. In addition, there is a need for methods for producing high quantities of such NERS-active structures at relatively low cost.

BRIEF SUMMARY OF THE INVENTION

The present invention, in a number of embodiments, includes NERS-active structures including features having nanoscale dimensions, methods for forming NERS-active structures, and methods for performing NERS using NERS-active structures.

A NERS-active structure is disclosed that includes at least one heterostructure nanowire having at least two active regions and at least one inactive region between the at least two active regions.

A method for performing NERS is disclosed that includes the steps of providing a NERS-active structure, placing an analyte adjacent the NERS-active structure, irradiating the analyte and the NERS-active structure with excitation radiation, and detecting Raman scattered radiation scattered by the analyte. The NERS-active structure includes at least one heterostructure nanowire having at least two active regions and at least one inactive region between the at least two active regions.

Also disclosed is a method for forming a NERS-active structure. The method includes providing a substrate, providing at least one catalyst nanoparticle, exposing the at least one catalyst nanoparticle to a gas comprising a first material to promote the formation of at least one nanowire of the first material, and exposing the at least one catalyst nanoparticle and the at least one nanowire to a gas comprising a second material to promote the formation of a heterostructure nanowire of the first material and the second material, wherein one of the first material and the second material comprises a NERS-active material and one of the first material and the second material comprises a NERS-inactive material.

Yet another method for forming a NERS-active structure includes providing a substrate, growing at least one nanowire of a first material on the substrate, coating the at least one nanowire with a second material to form at least one coated nanowire, coating the at least one coated nanowire with the first material to form at least one radial core-shell nanowire, embedding the at least one radial core-shell nanowire in a support matrix, and polishing the at least one radial core-shell nanowire and the support matrix to expose at least one multilayer ring.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes NERS-active structures including heterostructure nanowires which allow for improved enhancement of the Raman scattered signal intensity relative to conventional NERS-active structures, methods for forming NERS-active structures, NERS systems including NERS-active structures, and methods for performing NERS using such systems.

The term "NERS-active structure" as used herein means a structure that is capable of increasing the number of Raman-scattered photons that are scattered by a molecule when the molecule is located adjacent to the structure and the molecule and structure are subjected to electromagnetic radiation.

The term "NERS-active material" as used herein means a material that, when formed into appropriate geometries or configurations, is capable of increasing the number of Raman-scattered photons that are scattered by a molecule when the molecule is located adjacent the material and when the molecule and material are subjected to electromagnetic radiation. NERS-active materials can be used to form a NERS-active structure.

The term "nanoparticle" as used herein means a particle having cross-sectional dimensions of less than about 100 nanometers.

The term "analyte molecule" as used herein means a molecule upon which it is desired to perform NERS.

The term "heterostructure" as used herein means a structure in which materials having different compositions meet at interfaces.

It should be understood that the illustrations presented herein are not meant to be actual views of any particular NERS-active structure, but are merely idealized representations which are employed to describe the present invention. Additionally, elements common between FIGS. 1 through 7 retain the same numerical designation.

Figure 1A:
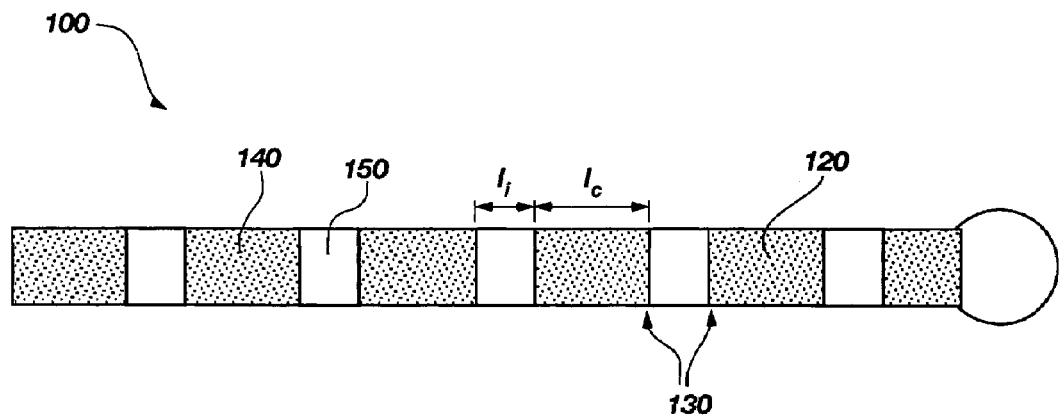
FIG. 1A illustrates a representative embodiment of a NERS-active structure according to the invention.

An exemplary embodiment of a NERS-active structure 100 according to the invention is shown in FIG. 1A. A NERS-active structure 100 includes a heterostructure nanowire 120 having a plurality of heterojunctions 130. Each heterojunction 130 comprises a location on the at least one heterostructure nanowire 120 where a region of conducting material 140 adjoins a region of an NERS-inactive material 150. The NERS-inactive material 150 may be, for example, a material with substantially smaller conductivity than the conductive region, or an NERS-inactive material.

The heterostructure nanowire 120 may be substantially cylindrical and have a diameter between about 5 and about 200 nanometers. Alternatively, the heterostructure nanowire 120 may be a longitudinal shape having faceted surfaces. The conducting region 140 may have a length $l_c$ between about 1 and about 50 nanometers, preferably between about 2 and about 20 nanometers. The NERS-inactive region 150 may have a length $l_i$ between about 0.1 and about 20 nanometers, preferably between about 0.5 and about 5 nanometers. In addition, length $l_i$ of the NERS-inactive region 150 may be selected to correspond to the size of a particular analyte molecule to be analyzed with the NERS-active structure 100, such that the molecule is capable of being adsorbed on the NERS-inactive region 150.

The conducting region 140 of the heterostructure nanowire 120 may include any NERS-active material such as, for example, gold, silver, copper, platinum, palladium, aluminum, or any other material that will enhance the Raman scattering of photons by analyte molecules positioned adjacent thereto. The NERS-inactive region 150 of the heterostructure nanowire 120 may be formed from any nonconductive material, including, but not limited to, silicon dioxide, silicon nitride, silicon oxynitride, or aluminum oxide.

Figure 1B:
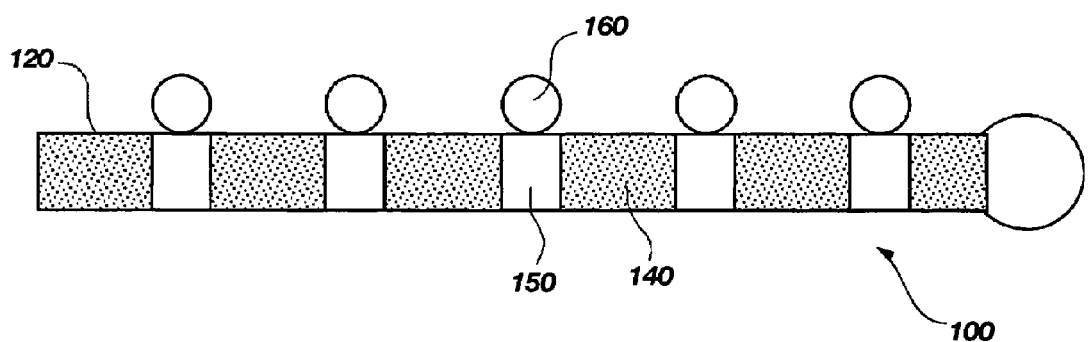
FIG. 1B illustrates the NERS-active structure of FIG. 1A with analyte molecules adsorbed thereon.

Analyte molecules 160, illustrated schematically in FIG. 1B, are shown adsorbed adjacent to NERS-inactive regions 150, and between the conducting regions 140 on the heterostructure nanowire 120.

Figure 2A:
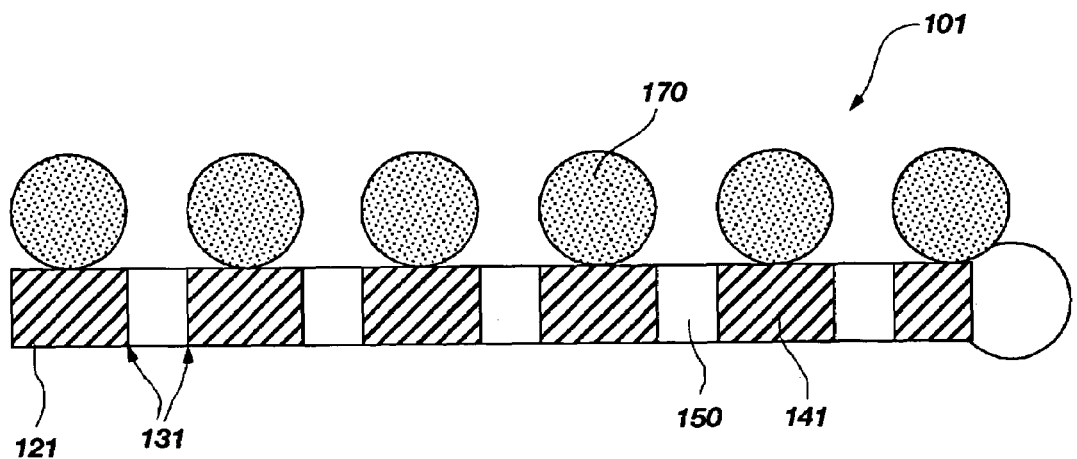
FIG. 2A illustrates another representative embodiment of a NERS-active structure according to the invention.

Another exemplary embodiment of a NERS-active structure 101 according to the invention is shown in FIG. 2A. A NERS-active structure 101 includes a heterostructure nanowire 121 having a plurality of heterojunctions 131. Each heterojunction 131 comprises a location on the at least one heterostructure nanowire 121 where a region of attracting material 141 adjoins a region of an NERS-inactive material 150. Nanoparticles 170 are positioned on the heterostructure nanowire 121 adjacent the attracting regions 141.

The attracting regions 141 of the heterostructure nanowire 120 may include a material capable of attracting nanoparticles 170 of a NERS-active material such as, for example, gold, silver, copper, platinum, palladium, aluminum, or any other material that will enhance the Raman scattering of photons by analyte molecules positioned adjacent thereto. Materials with functionalized surfaces may be suitable for the attracting regions 141. Functionalized surfaces are able to immobilize nanoparticles 170 thereon. The nanoparticles 170 may be preformed; alternatively, nanoparticles 170 may be formed on the attracting regions 141, for example by deposition. In another alternative, NERS active material may be deposited over substantially the entire heterostructure nanowire 120 and moved by thermal surface diffusion to a location over the attracting regions 141. Gold, for example, may be moved by thermal surface diffusion to a location over silicon attracting regions 141, with $SiO_2$ NERS-inactive regions 150 therebetween. The NERS-inactive region 150 of the heterostructure nanowire 120 may be formed from any material, including, but not limited to, silicon dioxide, silicon nitride, silicon oxynitride, or aluminum oxide.

Figure 2B:
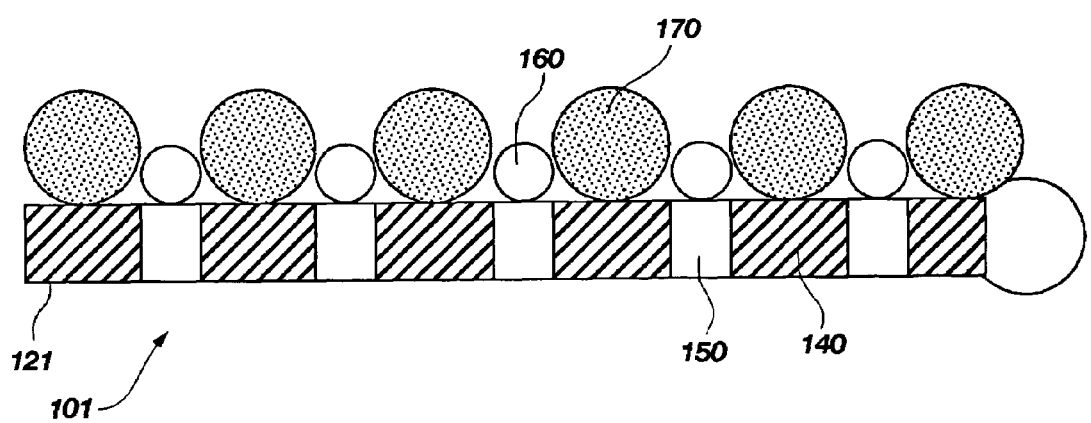
FIG. 2B illustrates the NERS-active structure of FIG. 2A with analyte molecules adsorbed thereon.

Analyte molecules 160, illustrated schematically in FIG. 2B, are shown adsorbed adjacent to NERS-inactive regions 150, and between the preformed nanoparticles 170 on the heterostructure nanowire 121.

Figure 3A:
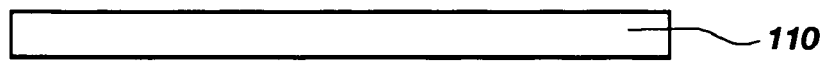
FIGS. 3A-3E illustrate a representative method for forming the NERS-active structures of FIGS. 1A and 2A.

An exemplary method for making the NERS-active structure 100 and the NERS-active structure 101 is illustrated in FIGS. 3A-3E. To produce the NERS-active structure 100, 101, a substrate 110 may be provided as shown in FIG. 3A. The substrate 110 may include a wafer or die of, for example, silicon or germanium, or III-V or II-VI semiconductor materials. The substrate may alternatively be formed from an NERS-inactive material, such as silicon dioxide or silicon nitride. Silicon dioxide on a silicon wafer is one example of an NERS-inactive substrate. Any suitable substrate material may be used, as long as the material does not fluoresce at the wavelengths corresponding to the Raman radiation emitted from the analyte employed in a NERS system. Next, heterostructure nanowires 120 are formed on a surface of the substrate 110. Various suitable methods for forming nanowires are known in the art of microdevice fabrication.

One process of forming heterostructure nanowires 120 in a <111> growth direction is the vapor-liquid-solid (VLS) process. This process involves dissolving gas reactants in nano-sized catalytic liquid followed by one-dimensional growth of single-crystalline nanowires. A molten metal droplet catalyzes the nanowire growth: vapor source materials are captured by the droplet, and then supersaturated atoms are deposited on the liquid-solid interface, forming a wire-shaped solid. The catalyst material may include, but is not limited to, gold, zinc, platinum, and palladium.

Figure 3B:
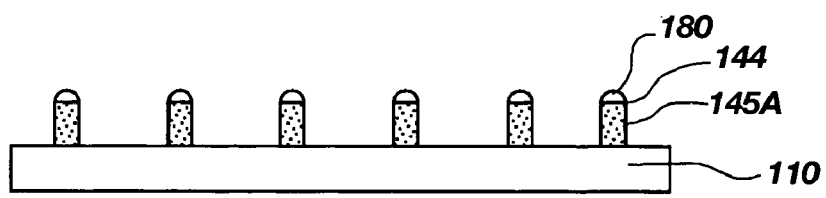
Figure 3C:
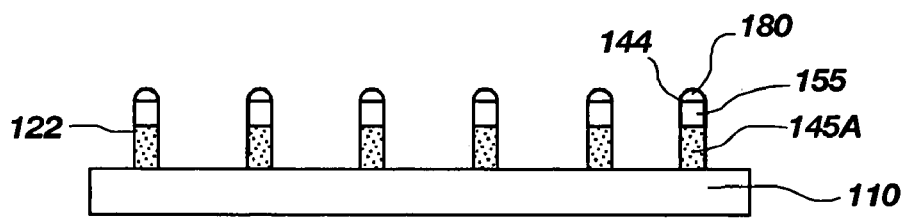
Figure 3D:
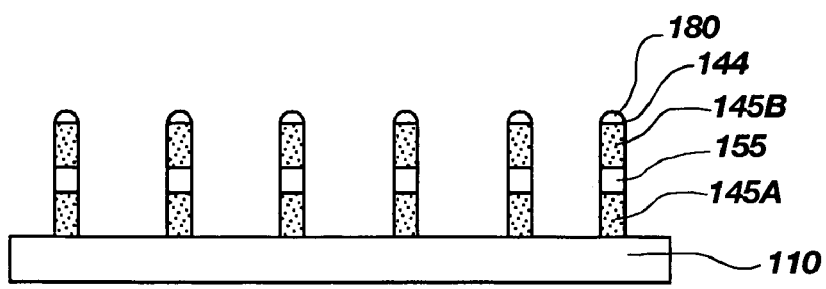
Figure 3E:
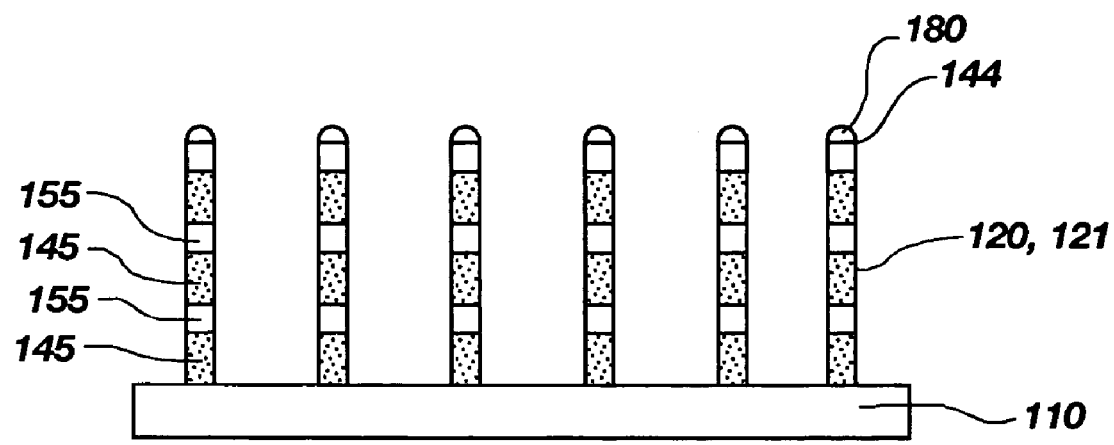

FIG. 3B illustrates nanowires of a first material 145A extending from a surface of the substrate 110 in a direction substantially perpendicular thereto. The nanowires 145A may be formed using a VLS process. The catalyst nanoparticles 180 cause the one-dimensional growth and remain at the terminus 144 of the wire-shaped solid being formed. The diameter of each nanowire 145A will be substantially the same as the catalyst nanoparticles 180. As shown in FIG. 3C, use of a different vapor source material enables a segment of a second material 155 to be grown from the end of each nanowire of the first material 145A, forming a plurality of heterostructure nanowires 122. FIG. 3D depicts a second segment 145B of the first material grown from the end of the heterostructure nanowires 122 of FIG. 3C. Continued growth of alternating segments of the first material 145 and the second material 155 forms the axial heterostructure nanowires 120, 121 with the catalyst nanoparticles 180 at the terminus 144 of each nanowire 120, 121, as shown in FIG. 3E.

The first material 145 may include any NERS-active material to form the heterostructure nanowire 120 of FIGS. 1A and 1B. The second material may be an NERS-inactive material. Alternatively, the first material may include a material capable of attracting preformed nanoparticles 170 of a NERS-active material to form the heterostructure nanowire 121 of FIGS. 2A and 2B. The length of each segment may be adjusted, for example, by the growth time of each material. Thus, a plurality of heterostructure nanowires may be formed with NERS-inactive regions 150 of a desired length so attracted preformed nanoparticles 170 may be separated by the desired distance.

Figure 4A:
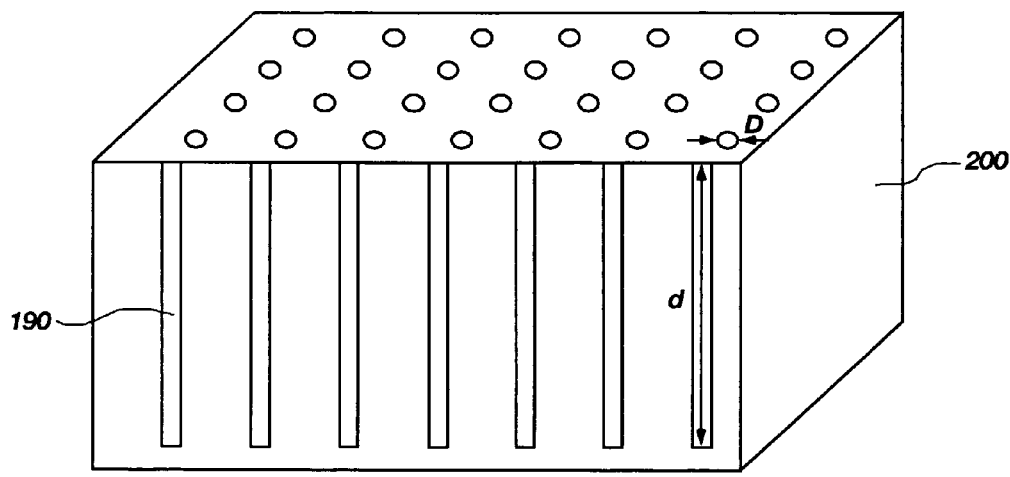
FIGS. 4A-4C illustrate another representative method for forming the NERS-active structures of FIGS. 1A and 2A.
Figure 4B:
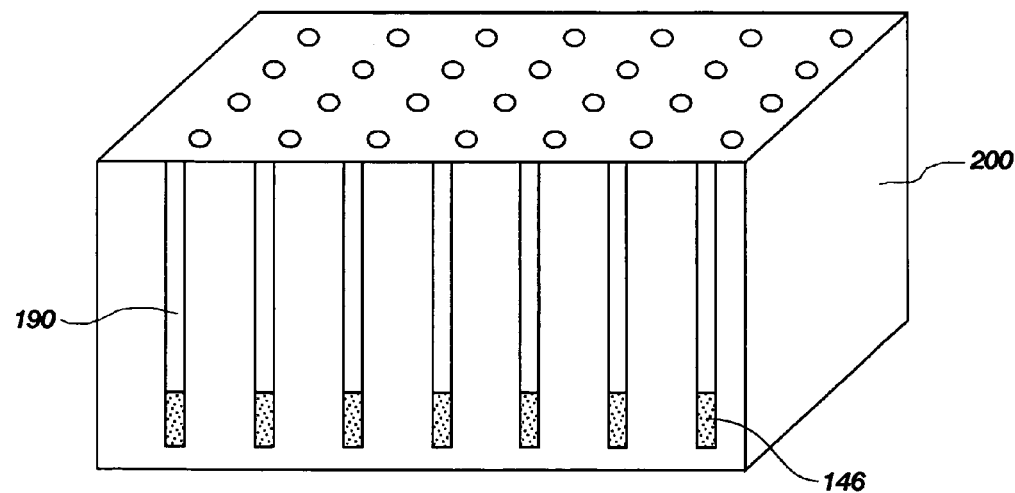
Figure 4C:
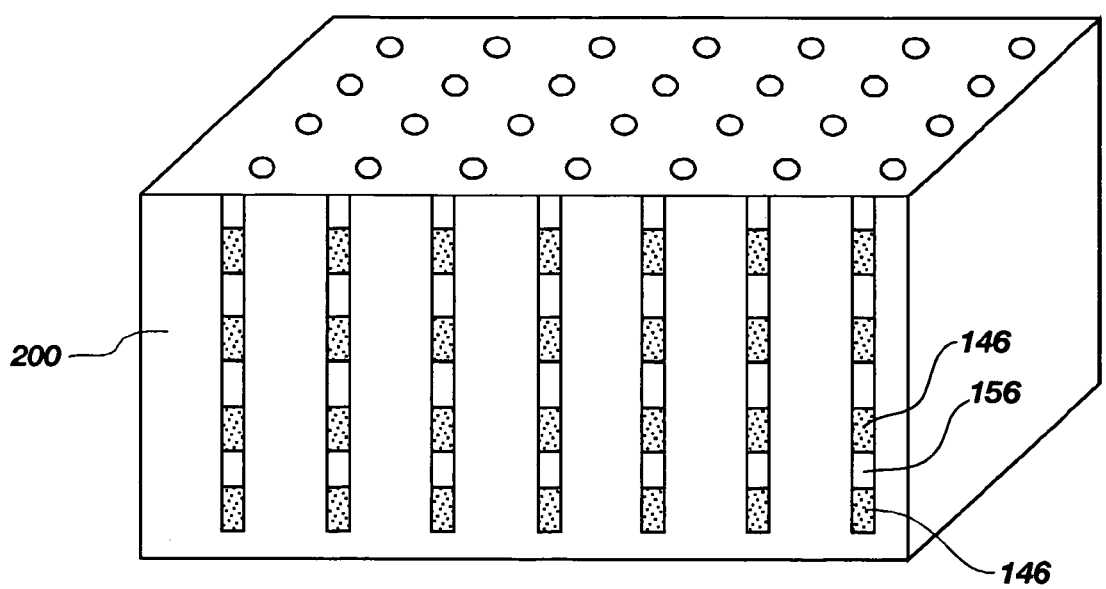

Another exemplary method for making the NERS-active structure 100 and the NERS-active structure 101 is illustrated in FIGS. 4A-4C. Nanopores may be filled to obtain the axial heterostructure nanowires 120, 121 of FIGS. 1A-2B. Nanopores 190 may be formed in a matrix or template 200 by nanoimprinting, or by an electrochemical process, such as anodic oxidation of a material such as aluminum. The template 200 may comprise, for example, alumina or polycarbonate.

The nanopores 190 may be substantially cylindrical and have a diameter D corresponding to the desired diameter of the heterostructure nanowires 120, 121 to be formed, for example, between about 5 and about 200 nanometers. The nanopores 190 may have a depth d corresponding to the desired length of the heterostructure nanowires 120, 121, for example, between about 5 nanometers and about 5 micrometers.

The nanopores 190 may be filled from the bottom as various materials are sequentially deposited within the nanopores 190. FIG. 4B illustrates a segment of a first material 146 within each nanopore 190. The segments of the first material 146 may be formed by electrodeposition or any suitable method. Electrodeposition within nanopores includes providing a plating bath, i.e. an electrolyte solution, and an electrical current. The nanopores 190 may extend completely through the template 200 when using electrodeposition, thus electrical connection to each nanopore 190 may be made.

After the segments of the first material 146 have reached the desired length, a different electrolyte solution may be introduced, and segments of a second material 156 may be formed by electrodepositing the second material 156 within the nanopores. The current flow may be halted while changing the electrolyte solution, and a different current may be utilized during the deposition of the second material 156.

Filling of the nanopores may continue, alternating the electrolyte solutions, and therefore the first material 146 and the second material 156 until the nanopores 190 are filled, as shown in FIG. 4C. The nanopores 190 are not necessarily completely filled, heterostructure nanowires 120, 121 having a length less than the depth d of the nanopores 190 are within the scope of the present invention. The first material may comprise any NERS-active material and the second material may comprise an NERS-inactive material, to form the structure of FIGS. 1A and 1B. The first material may also comprise a material capable of attracting nanoparticles of a NERS-active material, to form the structure of FIGS. 2A and 2B. Alternatively, the first material may comprise any NERS-inactive material and the second material may comprise an NERS-active material, to form the structure of FIGS. 1A and 1B.

The template material surrounding the heterostructure nanowires may be removed chemically, for example, by dissolving the template in methylene chloride if the template material is polycarbonate. Other suitable methods of releasing the heterostructure nanowires are within the scope of this invention. Once the surrounding template is released, the free-standing nanowires 120, 121 may be used as structures for NERS measurements, as described below. The nanowires 120, 121 may remain adhered to a substrate 110, for example, as shown in FIG. 3E, particularly where the nanopores 190 of the template 200 extend completely therethough.

Figure 5A:
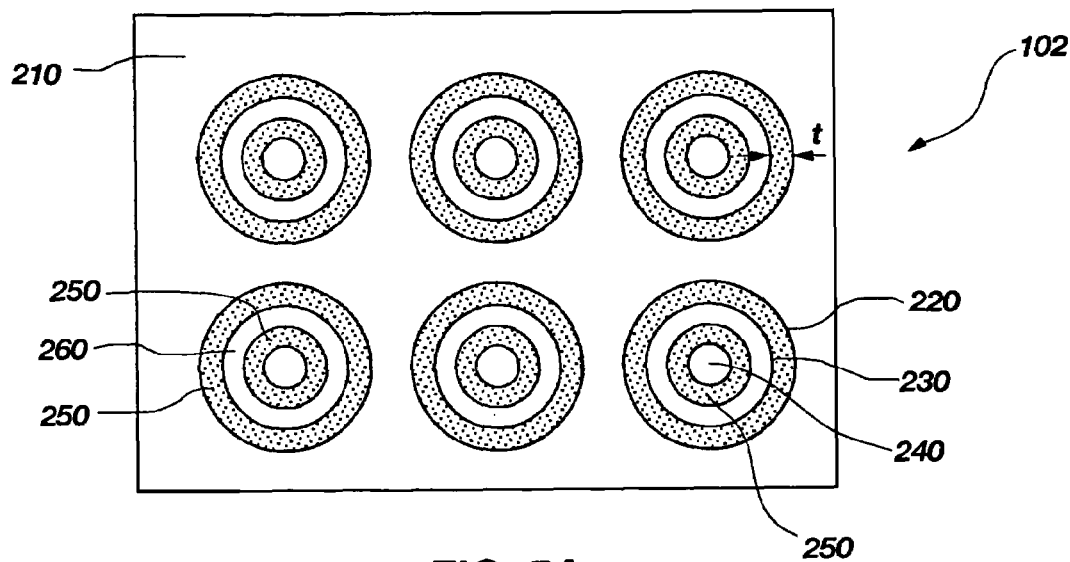
FIGS. 5A-5B depict another representative embodiment of a NERS-active structure according to the invention.

A third exemplary embodiment of a NERS-active structure 102 according to the invention is shown in FIG. 5A. The NERS-active structure 102 includes a heterostructure nanowire 220 having a plurality of heterojunctions 230. The heterostructure nanowire 220 may be a radial core-shell heterostructure, with a core 240 of a first material, and successive coatings 250, 260 of different materials. The material of one of the successive coatings 260 may comprise the first material of the core 240. The heterostructure nanowire 220 includes regions of material differing in the radial direction, and thus, ring-shaped heterojunctions 230 comprising interfaces wherein the materials having different compositions meet.

The heterostructure nanowires 220 may be embedded in a support matrix 210 comprising, for example, plasma-enhanced CVD (PECVD) silicon dioxide. The core 240 of the heterostructure nanowire 220 may comprise an NERS-inactive material. A coating 250 of the core 240 may include any NERS-active material, such as, for example, gold, silver, copper, platinum, palladium, aluminum, or any other material that will enhance the Raman scattering of photons by analyte molecules positioned adjacent thereto. Successive coatings 250, 260 of the core 240 may include alternating coatings of a NERS-active material and a NERS-inactive material. Alternatively, the core 240 of the heterostructure nanowire may comprise a NERS-active material, and coatings 250, 260 may alternate between an NERS-inactive material and a NERS-active material.

Figure 5B:
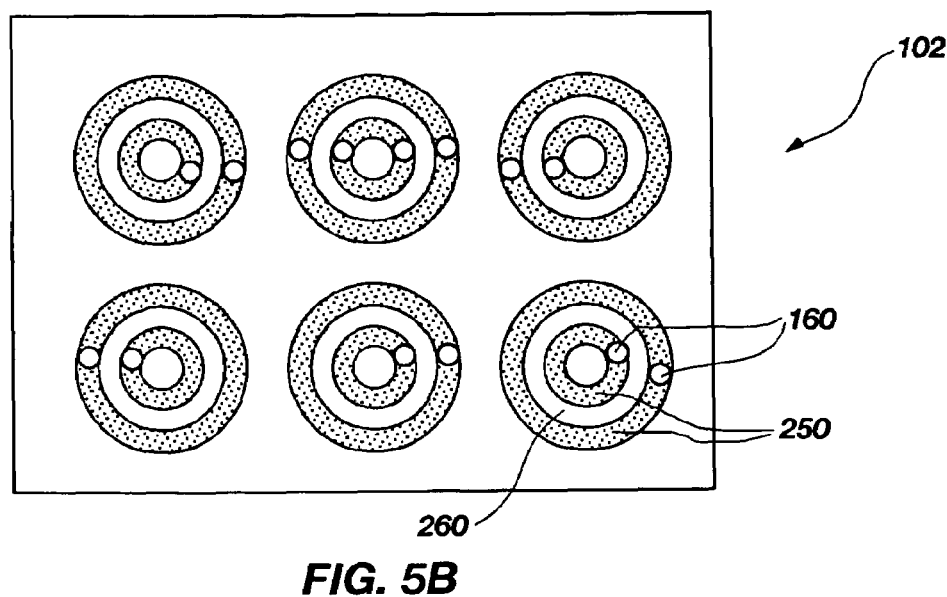

Analyte molecules 160, illustrated schematically in FIG. 5B, are shown adsorbed adjacent to coatings 250. The coatings 250 of FIG. 5B may comprise an NERS-inactive material, and the coatings 260 may comprise a NERS-active material. In another alternative, the coatings 250 may comprise a NERS-active material, the coatings 260 may comprise an NERS-inactive material, and the analyte molecules 160 can be adsorbed adjacent the coatings 260.

The heterostructure nanowire 220 may be substantially cylindrical and have a diameter between about 5 and about 200 nanometers. The core 240 of the heterostructure nanowire 220 also may be substantially cylindrical having a diameter of between about 1 and about 100 nanometers. Each coating 250, 260 of the nanowire 220 may have a thickness of between about 0.1 and about 50 nanometers. The thickness of the coating comprising an NERS-inactive material is preferably between about 0.5 and about 5 nanometers, and may be selected to correspond to the size of a particular analyte molecule to be analyzed with the NERS-active structure 102, such that the molecule is capable of adsorbing adjacent the coating of NERS-inactive material. The thickness of the coating comprising a NERS-active material is preferably between about 2 and about 20 nanometers.

Figure 5C:
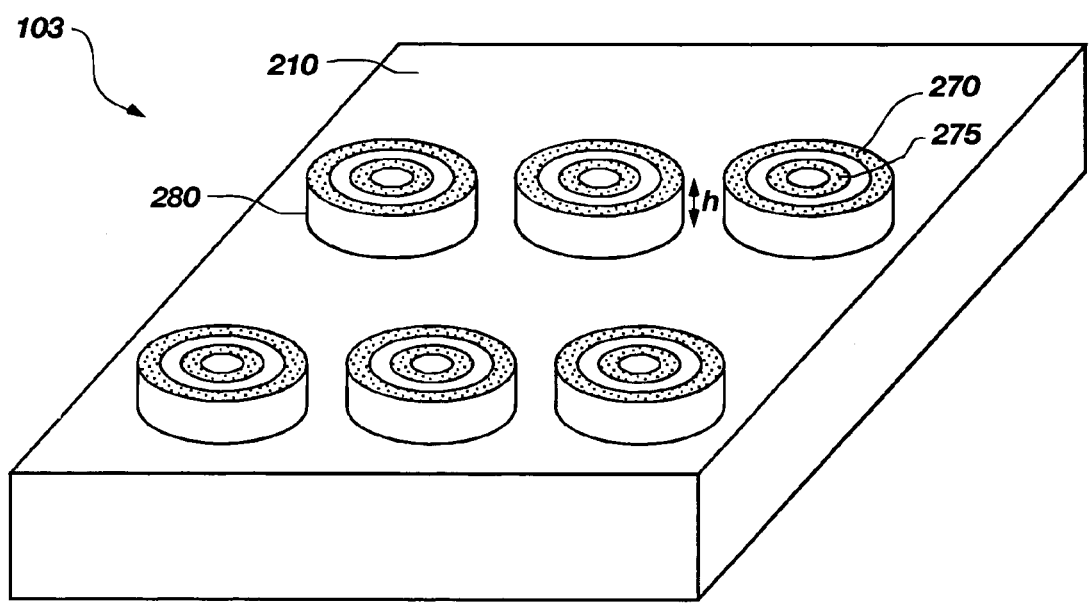
FIG. 5C depicts yet another representative embodiment of a NERS-active structure according to the invention.

A fourth exemplary embodiment of a NERS-active structure 103 according to the invention is shown in FIG. 5C. An array of features 280 are disposed on the support matrix 210. Each feature 280 comprises a inner cylindrical structure 275 and a concentric, hollow outer cylindrical structure 270 Each feature 280 may have a height h of between about 1 and about 50 nanometers. The inner cylindrical structure 275 and the outer cylindrical structure 270 may have a diameter of between about 1 and about 200 nanometers, and a thickness and spacing corresponding to the thickness and spacing of the coatings 250, 260 of the nanowires 220 of FIG. 5A.

The NERS-active structure 103 may be formed using the structure 102 of FIG. 5A, which may be formed as described below. The coatings 250 may be formed of a material, for example platinum, which may be used as a selective nucleation site for a NERS-active material, for example, gold, silver, copper, platinum, palladium, aluminum. The cylindrical structures 270, 275 may be grown using, for example, electroless deposition. Alternatively, the cylindrical structures 270, 275 may comprise a material capable of attracting nanoparticles of a NERS-active material, to form a NERS-active structure.

Figure 6A:
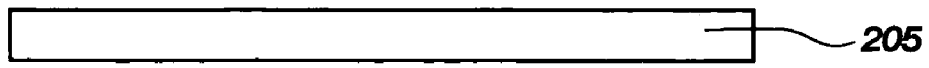
FIGS. 6A-6E illustrate a representative method for forming the NERS-active structures of FIGS. 5A and 5C.
Figure 6B:
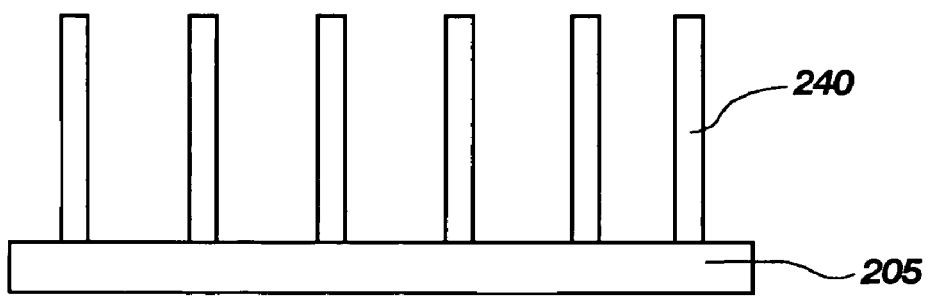

An exemplary method for making the NERS-active structures 102, 103 is illustrated in FIGS. 6A-6E. To produce the NERS-active structures 102, 103, a substrate 205 may be provided as shown in FIG. 6A. A plurality of nanowires 240 may be grown to the desired length on the substrate 205, illustrated in FIG. 6B. Any suitable method of growing nanowires may be used, such as, for example, chemical-vapor deposition (CVD). The nanowires may be grown in a CVD reactor (not shown). Catalyzed growth enables formation of the plurality of nanowires 240. For example, silicon nanowires may be grown by exposing the substrate to gases including $SiH_4$ or $SiH_2Cl_2$ at temperatures between about 500° C. and about 700° C. The catalyst material may cause the silicon-containing compounds to decompose and nanowire cores of silicon material may be grown in one dimension, forming the cores 240 of the nanowires 120, as shown in FIG. 6B. The length of the growing nanowire cores 240 may correspond to the duration of the reaction process.

Figure 6C:
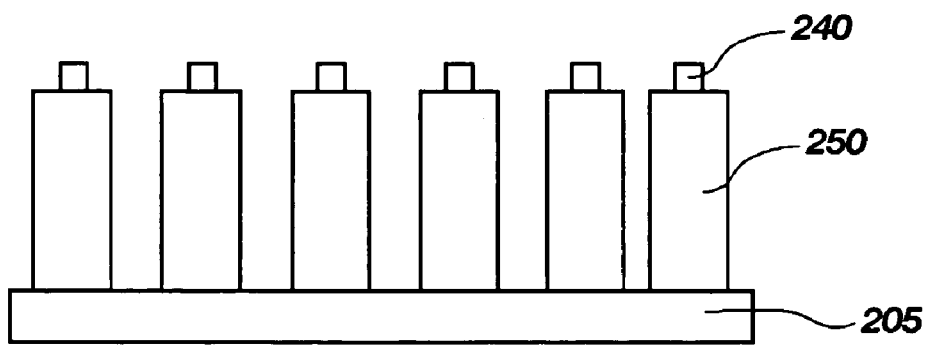

Changing conditions for non-catalyzed growth enables conformal coating of the nanowires 240 with layer or coating 250, as shown in FIG. 6C. The non-catalyzed growth may take place either in-situ, within the CVD reactor, or ex-situ. A plurality of coatings 250 may be provided. Altering the material of coatings 250 provides the alternating ring-shaped coatings 250, 260 as shown in FIG. 5A. The thickness of each coating 250, 260 may be controlled by altering the material deposited on the nanowires or cores 240 to form the plurality of core-shell nanowires 220.

Figure 6D:
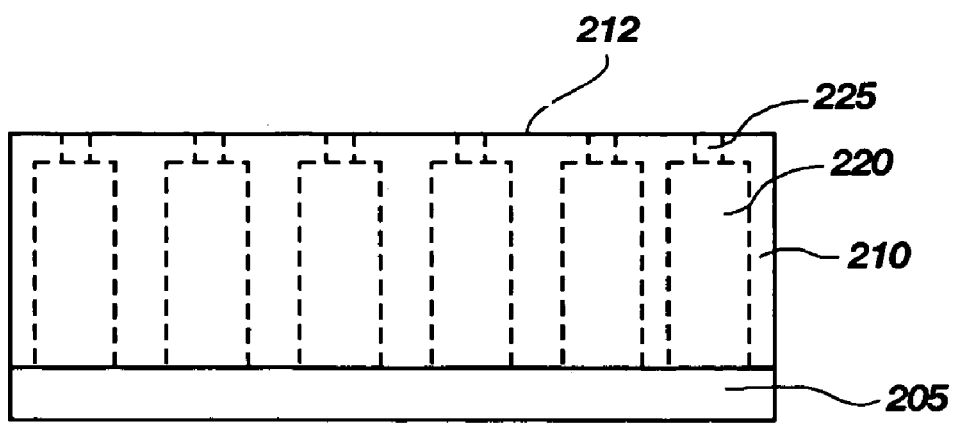

Referring to FIG. 6D, after the core-shell nanowires 220 have been formed, they may be embedded in the support matrix 210. The support matrix 210 may be deposited over the surface of the substrate 205, including the core-shell nanowires 220. The support matrix 210 may be formed by physical deposition techniques, including, but not limited to, sputtering, thermal evaporation, and electron beam evaporation, or chemical vapor deposition, including conformal chemical vapor deposition techniques, such as atomic-layer deposition (ALD). A surface 212 of the support matrix 210, and the distal tips 225 of the core-shell nanowires 220 may then be polished, for example, using chemical-mechanical polishing, ion milling, or mechanical polishing, to expose a surface 214 including the heterojunctions 230, as shown in FIG. 6E and in cross-section in FIG. 5A.

Figure 6E:
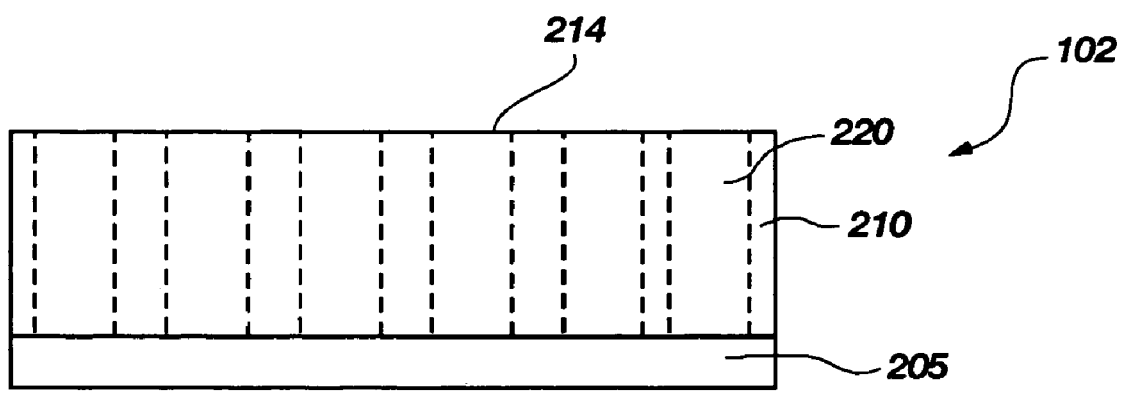

While the nanowires 120, 121, 220 are illustrated in FIGS. 3E and 6E as being of equal length and extending in parallel directions, the nanowires 120, 121, 220 may have varying lengths and may extend in nonparallel directions relative to other nanowires 120, 121, 220.

Figure 7:
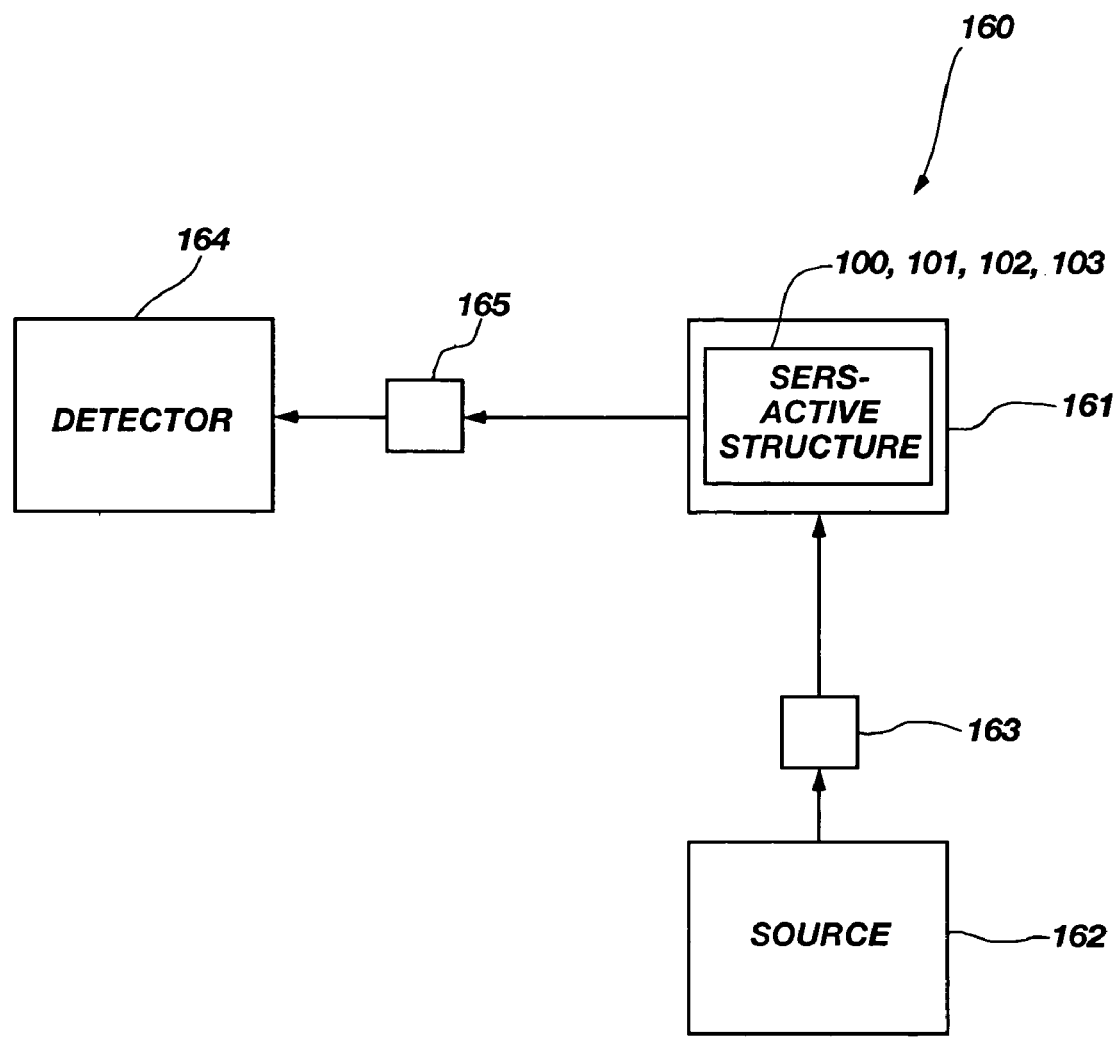
FIG. 7 is a schematic diagram of a system for performing nano-enhanced Raman spectroscopy using the NERS-active structures of FIGS. 1A, 2A, 5A, and 5C.

An exemplary NERS system 160 according to the invention is illustrated schematically in FIG. 7. The system 160 may include one of the exemplary NERS-active structures 100, 101, 102, 103, and may be used to perform nano-enhanced Raman spectroscopy. The NERS system 160 may include a sample or analyte stage 161, an excitation radiation source 162, and a detector 164. The analyte stage 161 may include one of the NERS-active structures 100, 101, 102, 103 (FIGS. 1A, 2A, 5A and 5C). The NERS system 160 also may include various optical components 163 positioned between the excitation radiation source 162 and the analyte stage 161, and various optical components 165 positioned between the analyte stage 161 and the detector 164.

The excitation radiation source 162 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation radiation source 162. The wavelengths that are emitted by the excitation radiation source 162 may include any suitable wavelength for properly analyzing the analyte using NERS. An exemplary range of wavelengths that may be emitted by the excitation radiation source 162 includes wavelengths between about 350 nm and about 1500 nm.

The excitation radiation emitted by the source 162 may be delivered either directly from the source 162 to the analyte stage 161 and the NERS-active structure 100, 101, 102, 103. Alternatively, collimation, filtration, and subsequent focusing of the excitation radiation may be performed by optical components 163 before the excitation radiation impinges on the analyte stage 161 and the NERS-active structure 100, 101, 102, 103.

The NERS-active structure 100, 101, 102, 103 of the analyte stage 161 may enhance the Raman signal of the analyte, as previously discussed. In other words, irradiation of the NERS-active structure 100, 101, 102, 103 by excitation radiation may increase the number of photons inelastically scattered by an analyte molecule positioned near or adjacent to the NERS-active structure 100, 101, 102, 103.

The Raman scattered photons may be collimated, filtered, or focused with optical components 165. For example, a filter or a plurality of filters may be employed, either as part of the structure of the detector 164 or as a separate unit that is configured to filter the wavelength of the excitation radiation, thus allowing only the Raman scattered photons to be received by the detector 164.

The detector 164 receives and detects the Raman scattered photons and may include a monochromator (or any other suitable device for determining the wavelength of the Raman scattered photons) and a device such as, for example, a photomultiplier for determining the quantity of Raman scattered photons (intensity).

Ideally, the Raman scattered photons are scattered isotropically, being scattered in all directions relative to the analyte stage 161. Thus, the position of the detector 164 relative to the analyte stage 161 is not particularly important. However, the detector 164 may be positioned at, for example, an angle of 90° relative to the direction of the incident excitation radiation to minimize the intensity of the excitation radiation that may be incident on the detector 164.

To perform NERS using the system 160, a user may provide an analyte molecule or molecules adjacent to the heterojunctions of the NERS-active structure 100, 101, 102, 103. The analyte and the NERS-active structure 100, 101, 102, 103 are irradiated with excitation radiation or light from the source 162. Raman scattered photons scattered by the analyte are then detected by the detector 164.

The structures and systems disclosed herein may also be used to perform enhanced hyper-Raman spectroscopy. When excitation radiation impinges on an analyte molecule, a very small number of photons may be scattered at frequencies corresponding to the higher order harmonics of the excitation radiation, such as the second and third harmonics (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

The methods disclosed herein allow for the reproducible formation of NERS-active structures including nanoscale features having well controlled size, shape, location, and orientation. These structures allow for improved nano-enhanced Raman spectroscopy and may be used to produce molecular sensors having superior sensitivity and uniformity relative to conventional Raman spectroscopy. The performance of nanoscale electronics, optoelectronics, molecular sensors, and other devices employing the Raman effect may be significantly improved by using the NERS-active structures disclosed herein. In addition, the methods disclosed herein allow for production of high quantities and high densities per substrate surface area of NERS-active structures at relatively low cost.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A NERS-active structure comprising at least one heterostructure nanowire having at least two active regions and at least one inactive region between the at least two active regions, wherein the at least one heterostructure nanowire comprises at least one radial core-shell heterostructure nanowire.

2. The NERS-active structure of claim 1, wherein the at least one radial core-shell heterostructure nanowire is embedded in a support matrix.

3. The NERS-active structure of claim 1, wherein the at least one radial core-shell heterostructure nanowire is substantially cylindrical, the at least one radial core-shell heterostructure nanowire having a diameter between about 5 nanometers and about 200 nanometers.

4. The NERS-active structure of claim 1, wherein the at least one inactive region is a coating having a thickness selected to correspond to the size of a particular analyte molecule to be analyzed with the NERS-active structure.

5. The NERS-active structure of claim 1 being incorporated into a system comprising:
 a light source configured to irradiate light onto the NERS-active structure; and
 a detector configured to receive Raman-scattered light scattered by an analyte located adjacent the NERS-active structure.

6. The NERS-active structure of claim 1, further comprising a plurality of heterostructure nanowires.

7. The NERS-active structure of claim 2, further comprising a substantially planar substrate affixed to the plurality of heterostructure nanowires.

8. A NERS-active structure, comprising:
 at least one heterostructure nanowire having at least two active regions and at least one inactive region between the at least two active regions, wherein the at least two active regions comprise at least two attracting regions, and the at least one inactive region is located between the at least two attracting regions, each attracting region configured to attract a nanoparticle; and
 at least two nanoparticles of NERS-active material, each nanoparticle positioned adjacent an attracting region.

9. The NERS-active structure of claim 8, wherein the at least one heterostructure nanowire comprises at least one axial heterostructure nanowire.

10. The NERS-active structure of claim 9, wherein the at least two active regions have a length between about 2 and about 20 nanometers.

11. The NERS-active structure of claim 10, wherein the at least one inactive region has a length between about 0.5 and about 5 nanometers.

12. The NERS-active structure of claim 11, wherein the length of the at least one inactive region is selected to correspond to the size of a particular analyte molecule to be analyzed with the NERS-active structure.

13. The NERS-active structure of claim 9, wherein the at least one axial heterostructure nanowire is substantially cylindrical, the at least one axial heterostructure nanowire having a diameter between about 5 nanometers and about 200 nanometers.

14. A method for performing NERS comprising:
 providing a NERS-active structure comprising:
  at least one heterostructure nanowire comprising:
   at least two active regions including:
    at least two attracting regions, each attracting region configured to attract a nanoparticle; and
    at least two nanoparticles of NERS-active material, each nanoparticle positioned adjacent an attracting region; and
   at least one inactive region between the at least two active regions;
 placing an analyte adjacent to the NERS-active structure;
 irradiating the analyte and the NERS-active structure with excitation radiation; and
 detecting Raman scattered radiation scattered by the analyte.

15. The method of claim 14, wherein the step of detecting comprises detecting Raman radiation scattered by a single molecule.

16. A method for forming a NERS-active structure, comprising:
 providing a substrate;
 providing at least one catalyst nanoparticle;
 exposing the at least one catalyst nanoparticle to a gas comprising a first material to promote the formation of an attracting region of at least one nanowire;
 exposing the at least one catalyst nanoparticle and the at least one nanowire to a gas comprising a second material to promote the formation of an inactive region of the at least one nanowire;
 exposing the at least one catalyst nanoparticle to the gas comprising the first material to promote the formation of an other attracting region of the at least one nanowire, thereby forming a heterostructure nanowire of the first material and the second material, wherein the first material is configured to attract nanoparticles of a NERS-active material and the second material comprises an NERS-inactive material; and
 depositing a nanoparticle of the NERS-active material on each of the attracting regions, thereby forming the NERS-active structure having at least two active regions with the inactive region positioned therebetween.

17. A method for forming a NERS-active structure, comprising:
 providing a substrate;
 growing at least one nanowire of a first active region material on the substrate;
 coating the at least one nanowire with a second inactive region material to form at least one coated nanowire;
 coating the at least one coated nanowire with the first active region material to form at least one radial core-shell heterostructure nanowire;
 embedding the at least one radial core-shell heterostructure nanowire in a support matrix; and
 polishing the at least one radial core-shell heterostructure nanowire and the support matrix to expose at least one multilayer ring.

18. The method of claim 17, wherein growing at least one nanowire comprises chemical vapor deposition of the first active region material.

19. The method of claim 17, wherein coating the at least one nanowire comprises chemical vapor deposition of the second inactive material.

20. The method of claim 17, further comprising growing a plurality of hollow cylindrical structures on the radial core-shell heterostructure nanowire.

* * * * *

UNITED STATES PATENT AND TRADEMARK OFFICE
CERTIFICATE OF CORRECTION

PATENT NO.       : 7,570,355 B2
APPLICATION NO.  : 11/341705
DATED            : August 4, 2009
INVENTOR(S)      : Theodore I. Kamins et al.

It is certified that error appears in the above-identified patent and that said Letters Patent is hereby corrected as shown below:

On the Title page, in Item (75), Inventors, in column 1, line 4, delete "Mountain View," and insert -- Sunnyvale, --, therefor.

In column 11, line 17, in Claim 7, delete "claim 2," and insert -- claim 6, --, therefor.

Signed and Sealed this

Twentieth Day of April, 2010

David J. Kappos
*Director of the United States Patent and Trademark Office*